(12) United States Patent
Markman

(10) Patent No.: US 7,455,979 B2
(45) Date of Patent: *Nov. 25, 2008

(54) POLYSACCHARIDE STRUCTURE AND SEQUENCE DETERMINATION

(75) Inventor: Ofer Markman, Rehovot (IL)

(73) Assignee: Procognia Ltd., Ashdod (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/403,507

(22) Filed: Apr. 12, 2006

(65) Prior Publication Data

US 2006/0194269 A1 Aug. 31, 2006

Related U.S. Application Data

(63) Continuation of application No. 09/979,610, filed as application No. PCT/IL00/00256 on May 4, 2000, now Pat. No. 7,056,678.

(30) Foreign Application Priority Data

May 6, 1999 (IL) .................................. 129835

(51) Int. Cl.
G01N 33/53 (2006.01)
(52) U.S. Cl. ................. 435/7.1; 435/74.5; 435/101; 435/183; 435/329; 436/151; 436/512; 436/572
(58) Field of Classification Search ............ 435/7.1, 435/101, 74.5, 183, 207–210, 329; 436/151, 436/512, 572, 164
See application file for complete search history.

(56) References Cited

U.S. PATENT DOCUMENTS

| | | | | |
|---|---|---|---|---|
| 5,888,757 A | * | 3/1999 | Kuranda | ............... 435/15 |
| 5,965,457 A | | 10/1999 | Magnani | ............... 436/518 |
| 6,197,599 B1 | | 3/2001 | Chin et al. | ............... 436/518 |
| 7,132,251 B1 | | 11/2006 | Markman et al. | ............... 435/18 |

FOREIGN PATENT DOCUMENTS

| | | |
|---|---|---|
| EP | 0 166 623 A2 | 1/1986 |
| EP | 0 421 972 A2 | 1/1991 |
| WO | WO 93/22678 | 11/1993 |
| WO | WO 93/24503 | 12/1993 |
| WO | WO 95/31177 | 11/1995 |
| WO | WO 97/35201 | 9/1997 |
| WO | WO 99/31267 | 6/1999 |
| WO | WO 00/68688 | 11/2000 |
| WO | WO 01/84147 | 11/2001 |
| WO | WO 02/37106 A3 | 5/2002 |

OTHER PUBLICATIONS

Andy et al. *J. Biol. Chem.*, 259(20):12844-12849 (1984).
Deng et al. *J. Biol. Chem.*, 269(13):9533-9538 (1994).
Galanina et al. *Tumor Biol.*, 19(Suppl. 1):79-87 (1998).
Goodarazi et al. *Glicoconjugate J.*, Abstract only, 14(4):493-496 (1997).
Hutchinson, A. *Anal. Biochem.* 220(2):303-307 (1994).
Knels et al. *J. Comp. Physiol. B*, 159: 629-639 (1989).
Laidler et al. *Int. J. Biochem. Cell Biol.*, 29(3):475-483 (1997).
Magnani, J. *Anal. Biochem.*, 150(1):13-17 (1985).
Rahman et al. *Microbial Pathogenesis*, 24:299-308 (1998).
Smith et al. *J. Biol. Chem.*, 262(25):12040-12047 (1987).
Yamashita et al. *Biochem.*, 27(15):5565-5573 (1988).
Yamashita et al. *Biochem.*, 29(12):3030-3039 (1990).
Alban, et al. (1992) "Synthesis of laminarin sulfates with anticoagulant activity". Arzneimittel Forschung. Drug Research 42(8):1005-8.
Chemical Abstract 105(19) (1986): "Preparation of oligosaccharides by gel filtration chromatography" Shengwu Huaxue Zazhi 2(3): 69-74 (Abstract only).
Chemical Abstracts 117(11) (1992): "The multiple attack of endo-1,3-beta-gluconase L-IV from the marine mollusk Spisula sachalinensis III. Evolution of the total distribution of laminarin hydrolysis products by glucanase L-IV and L0." Biokhimya 57(2): 275-8 (Abstract only).
Lepagnol-Descamps et al., (1998) "Purification and determination of the action pattern of Haliotis tuberculata laminarinase". Carbohydrate Research 310(4):283-9.
Read et al. (1996) "Analysis of the structural heterogeneity of laminarin by electrospray-ionisation-mass spectrometry". Carbohydrate Research 281(2):187-201.
Rosenfeld et al. (2003) *Glycobiol.*, Abastract, 13(11):845.

* cited by examiner

Primary Examiner—Long V. Le
Assistant Examiner—Changhwa J Cheu
(74) Attorney, Agent, or Firm—Ivor R. Elrifi; Erica R. Carlson; Mintz Levin Cohn Ferris Glovsky & Popeo PC

(57) ABSTRACT

The invention provides a method for the structural analysis of a saccharide, comprising: a) providing on a surface a plurality of essentially sequence- and/or site-specific binding agents; b) contacting said surface with a saccharide to be analyzed, or with a mixture comprising a plurality of fragments of said saccharide; c) washing or otherwise removing unbound saccharide or saccharide fragments; d) adding to the surface obtained in step c) an essentially sequence- and/or site-specific marker, or a mixture of essentially sequence- and/or site-specific markers; e) acquiring one or more images of the markers that are bound to said surface; and f) deriving information related to the identity of the saccharide being analyzed from said image.

21 Claims, 3 Drawing Sheets

A

B

C

D

E

Lectin#

POLYSACCHARIDE STRUCTURE AND SEQUENCE DETERMINATION

RELATED APPLICATIONS

This application is a continuation of U.S. patent application Ser. No. 09/979,610, filed May 21, 2002, which is a national stage application, filed under 35 U.S.C. §371, of International Application No. PCT/IL00/00256, filed on May 4, 2000, which claims the benefit of and priority to IL Application No. 129835, filed May 6, 1999. The contents of these applications are each incorporated herein by reference in their entirety.

FIELD OF THE INVENTION

This invention relates to the field of structural analysis of saccharide chains, such as those that occur either attached to proteins (proteoglycans, glycoproteins) or lipids, or as free saccharides.

INTRODUCTION

Oligosaccharides and polysaccharides consist of monosaccharide (sugar) units that are connected to each other via glycosidic bonds. The saccharide chain has, like a chain of DNA or protein, two dissimilar ends. In the case of saccharide chains, these are the reducing end (corresponding to the aldehyde group of the linear sugar molecule) and the non-reducing end. Unlike proteins and DNA, however, saccharides may also be branched, with essentially each of the sugar units in the saccharide serving as an optional branching point.

There are a number of proteins that bind to saccharides. Many of these proteins bind specifically to a certain short oligosaccharide sequence. Lectins are proteins isolated from plants that bind saccharides. For the purpose of this application, the term "lectin" also encompasses saccharide-binding proteins from animal species (e.g. "mammalian lectins"). Antibodies are proteins that specifically recognize certain molecular structures. Antibodies may also recognize saccharide structures, as do lectins. Glycosidases are enzymes that cleave glycosidic bonds within the saccharide chain. Also glycosidases may recognize certain oligosaccharide sequences specifically. Glycosyltransferases are enzymes that cleave the saccharide chain, but further transfer a sugar unit to one of the newly created ends.

The art of structural determination of polysaccharides has not developed as rapidly as the art of protein analysis and DNA analysis. This is due to the fact that in the wake of fundamental discoveries in the field of DNA-related research, it was recognized that the importance of DNA had been grossly underestimated. This resulted in several decades of intense research into DNA analysis methods and into DNA itself. Moreover, with the advent of ever improved and simplified DNA analysis methods, the art of protein structure and function analysis began to use more and more DNA-technology derived tools. For instance, the structural determination of a protein is usually carried out by reverse genetic techniques, e.g. obtaining a small fraction of the protein sequence and deducing the remaining protein amino acid sequence from the corresponding mRNA sequence, which is today easily available in most cases, as a large part of the mRNA sequences of a number of species, including human, are available in databases.

The analysis of a very important part of most mammalian proteins, i.e. of their attached saccharides and glycans, has been generally slower compared to the advance made in DNA and protein analysis technology.

The importance of glycomolecules is highlighted by the discovery of penicillin, an inhibitor of glycomolecule synthesis in the bacterial cell-wall and possibly the most successful antibiotic discovered to date.

Another example is the medical use of Heparin, a glycan that inhibits blood clotting and is today widely used in medicine. Further examples of medically-important glycomolecules include: glycosaminoglycans (GAGs), heparan sulphate, cytokines (e.g. IL-8, TNF), chemokines (e.g. acidic fibroblast growth factor) and various growth factors. The aforementioned cytokines, chemokines and growth factors are also capable of binding to GAGs and other polysaccharides, and therefore they may also be considered to be lectins.

The structural determination of polysaccharides is of fundamental importance for the development of glycobiology. Research in glycobiology relates to subjects as diverse as the above-mentioned bacterial cell walls, blood glycans, to growth factor and cell surface receptor structures involved in viral disease, such as HIV infection, autoimmune diseases such as Insulin dependent diabetes and Rheumatoid arthritis, and abnormal cell growth as it occurs in cancer.

In other fields of medicine, like the provision of contact lenses, artificial skin, development of prostheses, polysaccharides are good candidate materials. Furthermore, polysaccharides are used in a number of non-medical fields, such as the paper industry. Additionally, of course, the food and drug industry uses large amounts of various polysaccharides and oligosaccharides.

In all of the above fields, there is a need for improved saccharide analysis technologies, for the purposes of quality control, structure determination in research, and for conducting structure-function analyses.

Advanced analysis methods have been introduced in the fields of protein and DNA sequencing a number of years ago. The components that make up DNA and proteins are connected to each other by only one kind of connection (the 5' to 3' phosphoric acid bridge in DNA, and the peptide bond in proteins). DNA contains only four different components (the nucleic acids), while proteins contain about 20 different components (the amino acids). Although modified amino acids exist, a protein must first be synthesized, according to the genetic code, by using a DNA template. Therefore, the number and kind of amino acids that exist in a newly synthesized protein is restricted to the limited repertoire of amino acids represented in the genetic code. This code is universal, with only minor differences, for all life forms.

For the above structural reasons, the structural analysis of proteins and of DNA is today a simple, rapid, and relatively cheap procedure that does not require highly skilled personnel.

In contrast, a multitude of methods for the analysis of saccharide structures have been developed, each with its own shortcomings. It is today not possible, independent of the degree of sophistication of the method used, to determine the entire sequence of a polysaccharide or even of an oligosaccharide by using a single technique. There are several reasons for this difficulty. First, saccharides are synthesized template-independent. In the absence of structural information, the researcher must therefore assume that the building units are selected from any of the saccharide units known today. In addition, these units may have been modified, e.g. by the addition of sulfate groups, during synthesis.

Second, the connections between saccharide units are multifold. A saccharide may be connected to any of the C1, C2, C3, C4, or C6 atom if the sugar unit it is connected to is a hexose. Moreover, the connection to the C1 atom may be in either α or β configuration.

Thirdly, saccharides may be branched, which further complicates their structure and the number of possible structures that have an identical number and kind of sugar units.

A fourth difficulty is presented by the fact that the difference in structure between many sugars is minute, as a sugar unit may differ from another merely by the position of the hydroxyl groups (epimers).

THE PRIOR ART

A number of methods for the structural analysis of saccharides have been developed.

WO 93/24503 discloses a method wherein monosaccharide units are sequentially removed from the reducing end of an oligosaccharide by converting the monosaccharide at the reducing end to its keto- or aldehyde form, and then cleaving the glycosidic bond between said monosaccharide and the next monosaccharide in the oligosaccharide chain by using hydrazine. The free monosaccharides are separated from the oligosaccharide chain and identified by chromatographic methods. The process is then repeated until all monosaccharides have been cleaved.

WO 93/22678 discloses a method of sequencing an unknown oligosaccharide by making assumptions upon the basic structure thereof, and then choosing from a number of sequencing tools (such as glycosidases) one which is predicted to give the highest amount of structural information. This method requires some basic information as to the oligosaccharide structure (usually the monosaccharide composition). The method also illustrates the fact that reactions with sequencing reagents are expensive and time-consuming, and therefore there is a need for a method that reduces these expenses.

WO 93/22678 discloses a method for detecting molecules by probing a monolithic array of probes, such as oligodeoxynucleotides, immobilized on a VLSI chip. This publication teaches that a large number of probes can be bound to an immobilized surface, and the reaction thereof with an analyte detected by a variety of methods, using logic circuitry on the VLSI chip.

EP 421,972 discloses a method for sequencing oligosaccharides by labeling one end thereof, dividing the labeled oligosaccharide into aliquots, and treating each aliquot with a different reagent mix (e.g. of glycosidases). pooling the different reaction mixes, and then analyzing the reaction products, using chromatographic methods. This method is useful for N-linked glycans only, as they have a common structure at the point where the saccharide chain is linked to the protein. O-linked glycans are more varied, and the method has as yet not been adapted for such oligosaccharides with greater variability in their basic structure.

It is therefore an object of the invention to provide a method for the structural analysis of saccharides which overcomes all of the problems associated with the above prior art methods.

Thus, the invention provides the above structural analysis of saccharides by a single technique, without the need to combine results obtained with different techniques in order to achieve a final result.

The method of the present invention is suitable for the structural analysis of oligosaccharides, as well as of polysaccharides.

The method of the present invention is further suitable for automation, and thus provides a simple and rapid assay providing essentially enough information to uniquely identify a given oligo-or polysaccharide.

The present invention further provides a method for identifying the sequence of a given oligo-or polysaccharide.

Further objects and advantages of the invention will become clear as the description proceeds.

SUMMARY OF THE INVENTION

The invention is primarily directed to a method for the structural analysis of a saccharide, comprising:
   a) providing on a surface a plurality of essentially sequence-specific and/or site-specific binding agents;
   b) contacting said surface with a saccharide to be analyzed, or with a mixture comprising a plurality of fragments of said saccharide;
   c) washing or otherwise removing unbound saccharide or saccharide fragments;
   d) adding to the surface obtained in step (c) an essentially sequence- and/or site-specific marker, or a mixture of essentially sequence- and/or site-specific markers;
   e) acquiring one or more images of the markers that are bound to said surface; and
   f) deriving information related to the identity of the saccharide being analyzed from said image.

In a preferred embodiment of the method of the invention, the essentially sequence- and/or site-specific markers are chromogenic binding agents. The term "chromogenic binding agent" as used herein includes all agents that bind to saccharides and which have a distinct color or otherwise detectable marker, such that following binding to a saccharide, said saccharide acquires said color or other marker. In addition to chemical structures having intrinsic, readily-observable colors in the visible range, other markers used include fluorescent groups, biotin tags, enzymes (that may be used in a reaction that results in the formation of a colored product), magnetic and isotopic markers, and so on. The foregoing list of detectable markers is for illustrative purposes only, and is in no way intended to be limitative or exhaustive. In a similar vein, the term "color" as used herein (e.g. in the context of step (e) of the above described method) also includes any detectable marker.

In a preferred embodiment of the method of the invention, the structural information is obtained by simple visual inspection of the surface and comparison with a standard. Alternatively, in another preferred embodiment, step (f) comprises the use of optical filters. In a further preferred embodiment, the image of the colors that develop on the surface is captured by photography and then digitized.

Although the method of the invention may be performed using any suitable essentially sequence-specific binding agent, the invention is particularly directed to the use of lectins as essentially sequence- and/or site-specific binding agents. In another preferred embodiment of the invention, the essentially sequence- and/or site-specific binding agents are antibodies.

Any suitable colored (or otherwise detectable) substance that binds to saccharides in an essentially sequence- and/or site-specific manner may be used as an essentially sequence-and/or site-specific chromogenic binding agent. Generally, however, the essentially sequence- and/or site-specific chromogenic binding agent is a chromogenic lectin or chromogenic antibody. In one preferred embodiment of the invention, the chromogenic binding agent is a colored lectin. Further preferred embodiments call for the use of fluorescent or biotin-labeled lectins or antibodies. In yet a further preferred embodiment, the essentially sequence-specific chromogenic binding agent is an enzyme-labeled antibody.

In another aspect, the method of the invention further comprises treating the saccharide with an essentially sequence-specific agent capable of cleaving the saccharide chain after binding thereto. This treatment may be performed before the saccharide is contacted with the surface. Alternatively, the treatment may be performed after removal of unbound saccharide, but before adding the essentially sequence-specific chromogenic binding agents.

In a particularly preferred embodiment of the method of the invention, the surface is a filter paper, and the essentially sequence-specific agents are arranged in a pre-defined order on said filter paper.

In another aspect, the invention provides a glycomolecule identity (GMID) card, listing saccharide structural analysis data obtained according to the immediately preceding preferred embodiment of the method of the invention. In a preferred embodiment, the essentially sequence-specific reagents used are represented on the GMID card by code numbers. In another preferred embodiment of the GMID card, combinations of essentially sequence-specific reagents used in the analysis are represented by unique code numbers.

The invention is also directed to a solid support comprising in a pre-defined order a plurality of visual or otherwise detectable markers representative of a saccharide or saccharide sequence or fragment.

In another aspect, the invention also encompasses a method for choosing a set of essentially sequence-specific chromogenic binding agents for use in the above-described method, comprising the steps of:
 a) obtaining the full or partial monosaccharide composition (MC) of the saccharide to be analyzed;
 b) choosing a set of n essentially sequence- and/or site-specific markers that are capable of binding to the monosaccharides present in said saccharide;
 c) revising the set of essentially sequence- and/or site-specific markers obtained in step b) in order to ensure that no two markers in said set have the same color or otherwise detectable marker;
 d) revising the set of essentially sequence- and/or site-specific markers chosen in step c) in order to reduce cross-reactivity with either the essentially sequence- and/or site-specific binding agents or with other essentially sequence- and/or site-specific markers.

In one preferred embodiment of this method, the MC of the saccharide to be analyzed is estimated from the MC of a related saccharide. In another preferred embodiment, the MC of the saccharide to be analyzed is obtained by performing a complete MC analysis of said saccharide. In another preferred embodiment of this method, n has a value between 1 and 4.

The present invention is also directed to software for choosing a set of essentially sequence-specific markers for use in the above-described method of saccharide structural analysis, comprising:
 a) input for providing the monosaccharide composition (MC);
 b) matching sub-program to match n essentially sequence- or site-specific markers that are capable of binding to the monosaccharides present in said saccharide;
 c) revising sub-program to revise a set of essentially-sequence- or site-specific markers matched by sub-program b), said sub-program being capable of selecting said markers on the basis of reduced cross-reactivity with either the essentially sequence- or site-specific binding agents or with other essentially sequence- or site-specific markers;
 d) second revision sub-program being capable of ensuring that not two markers in said set have the same color or otherwise detectable feature.

This invention also relates to a method for obtaining structure-related data of saccharides, comprising, in any order, the steps of
 a) reacting the saccharide with a essentially sequence-specific agent capable of cleaving the saccharide chain,
 b) reacting the saccharide with an essentially sequence-specific agent capable of binding to the saccharide,
 c) introducing a label into the saccharide, by either directly or indirectly including the use of a labeled essentially sequence-specific agent capable of binding the saccharide, and
 d) detecting the presence of the label in reactions where the cleavage agent was present and in reactions where the cleavage agent was not present.

The invention further relates to a method for the structural analysis of saccharides, comprising the steps of:
 a) providing a saccharide;
 b) reacting said saccharide with a first essentially sequence-specific agent;
 c) reacting the saccharide or fragment thereof with a second essentially sequence-specific agent,
 d) reacting the saccharide or fragment thereof with a third essentially sequence-specific agent,
 e) optionally, repeating steps c to d using at least one different second or third essentially sequence-specific agent;
 wherein steps a) to e) may be carried out using the same saccharide in parallel independent reactions, using at least one different first, second, or third essentially sequence-specific agent,
 with the proviso that the saccharide is labeled and/or one or more of the said first, second, and/or third essentially sequence-specific agents is labeled or introduces a label to the saccharide, and the label is detected at one or more of the steps subsequent to the step wherein it is introduced, and with the further proviso that at least one of the first, second or third essentially sequence-specific agents is a cleaving agent. The label is preferably a fluorescent label.

The invention also relates to said method wherein at least one of the first, second, or third essentially sequence-specific agents is immobilized, wherein said immobilized agent is not the essentially sequence-specific agent which is the cleavage agent.

Further comprised within the scope of the invention is said method wherein the first essentially sequence-specific agent is a cleavage agent.

Also comprised within the scope of the invention is said method wherein the second essentially sequence-specific agent is immobilized. In a preferred embodiment, the cleavage agent may be a glycosidase or glycosyltransferase, the second essentially sequence-specific agent is a lectin, and the third essentially sequence-specific agent is an antibody.

In a preferred embodiment, the third essentially sequence-specific agent is a lectin. Further comprised within the scope of the invention is said method, wherein the third essentially sequence-specific agent is a cleavage agent.

The invention also relates to said method which further comprises the step of deducing the sequence of the saccharide.

The invention further relates to said method wherein the third essentially sequence-specific agent is a glycosidase or glycosyltransferase.

In a preferred embodiment of the above method of the invention, a number of the first sequence-specific agents are immobilized on the same substrate. Preferably, all first sequence-specific agents are immobilized on a single substrate.

The first essentially sequence-specific agents used in the method of the invention are preferably selected from lectins and antibodies. The second or third essentially sequence-specific agent is preferably a glycosyltransferase that introduces a labeled monosaccharide unit onto the saccharide.

In another preferred embodiment of said method, more than one label is used and each of the labels used is detectable independently.

The invention also relates to said method wherein the second and third essentially sequence-specific agents are present at the same time in the reaction, but are activated one after the other by a change in buffer conditions, so that one of said essentially sequence-specific agents is inactivated by that change, while the other essentially sequence-specific agent is activated.

Further preferably, several third essentially sequence-specific agents may be added simultaneously, but are activated one after the other by a change in buffer conditions, so that one or more of said essentially sequence-specific agents is inactivated by that change, while another essentially sequence-specific agent is activated. Preferably, one or more of the third essentially sequence-specific agents are glycosidases or glycosyltransferases.

The invention also relates to said method wherein each of the first or second essentially sequence-specific agents is immobilized on a separate unit in a virtual array. The array is preferably a MASDA array.

Further, the invention relates to a method for analyzing the structure of a saccharide by sequential digestion using a glycosidase, or an equivalent thereof. In a preferred embodiment, the method analyzing the structure of a saccharide by sequential digestion comprises the steps of a) blocking the reducing end of the saccharide;
b) exposing a further reducing end by incubation of said saccharide with a glycosidase, or an equivalent thereof,
c) labeling said further reducing end,
d) optionally, repeating steps a-c using different glycosidases, or equivalents thereof.

Still further, the invention relates to a method of analyzing the structure of a saccharide as described further above, wherein data are gathered according to the above described method for obtaining structure-related data of saccharides and said data are used in combination to therefrom derive structural information on the saccharide.

The invention also relates to a method of creating a sequence map of a saccharide, using data obtained according to the above described method for obtaining structure-related data of saccharides, comprising the steps of a) collecting triplets of recognition sequences, using the above method
b) identifying triplets of type 1, which triplets are triplets of the sequence (first recognition site)-(glycosidase)-(second recognition site),
c) identifying triplets of type 2, which triplets are triplets of the sequence (glycosidase)-(first recognition site)-(second recognition site),
d) sorting said triplets according to similarity,
e) comparing triplets with different glycosidase recognition sites,
f) arranging the triplets in the order of occurrence on the saccharide,
g) arranging the glycosidase recognition sites,
h) checking the compatibility to the triplets,
i) arranging recognition sequences of glycosidases and of first and second essentially sequence-specific agents in a single file order, and
j) translating the recognition sequences (sites) into polysaccharide sequence.

Further, the invention relates to a method of creating a sequence map of a saccharide, which further comprises the steps of k) correcting overlap problems
l) outputting a sequence
m) checking against all available data, to thereby create a model of the actual saccharide sequence.

The invention also relates to said of creating a sequence map of a saccharide, wherein step m) comprises checking against additional obtained according to the above method for obtaining structure-related data of saccharides, thereby further creating a sequence map of the saccharide.

The invention also relates to an apparatus for analyzing the structure of a saccharide, providing an array of first essentially sequence-specific agents in a planar structure, so that each first essentially sequence-specific agent is located in a certain area of said planar structure, further providing means for reacting analyte with the array, washing means, means for reacting one or more second and third essentially sequence-specific agents with the array, and detection means for detecting a label associated with the saccharide or the second or third essentially sequence-specific agents.

In another aspect, the invention provides an apparatus for analyzing the structure of a saccharide, having a multitude of aliquots of beads, each aliquot carrying a different first essentially sequence-specific agent, further providing means for reacting analyte with the aliquots of beads separately, washing means, means for reacting one or more second and third essentially sequence-specific agents with the aliquots, and detection means for detecting a label associated with the saccharide or the second or third essentially sequence-specific agents.

The methods of the invention may be used to investigate the structure of oligo- or polysaccharides. They may also be used when such oligo- or polysaccharides are coupled to other molecules, e.g., peptides, proteins, or lipids. Specifically, the method of the invention may be used for the structural investigation of glycosaminoglycans (GAGs), including heparin, heparan-sulphate, chondroitin-sulphate, dermatan-sulphate and the like.

All the above and other characteristics and advantages of the invention will be further understood from the following illustrative and non-limitative examples of preferred embodiments thereof.

BRIEF DESCRIPTION OF THE DRAWINGS

The present invention will be more clearly understood from the detailed description of the preferred embodiments and from the attached drawings in which.

DETAILED DESCRIPTION OF THE INVENTION

Figure 1:
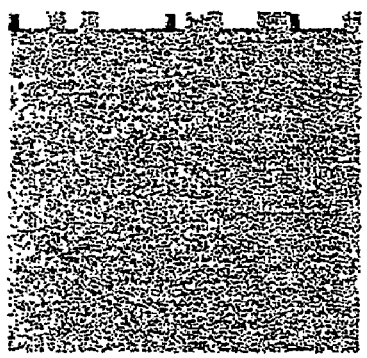
FIG. 1 is an illustration of the Glycomolecule identity (GMID) cards obtained for pasteurized goat's milk (A and B), non-pasteurized goat's milk (C and D) and bovine milk (E).
Figure 1:
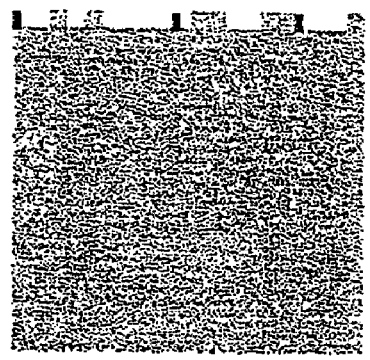
Figure 1:
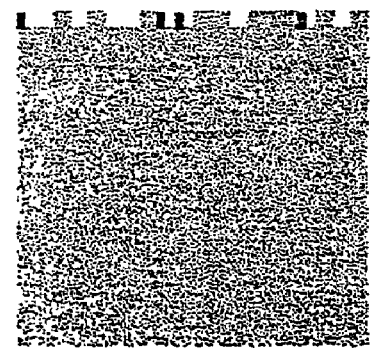
Figure 1:
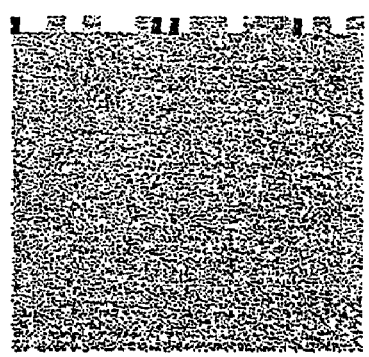
Figure 1:
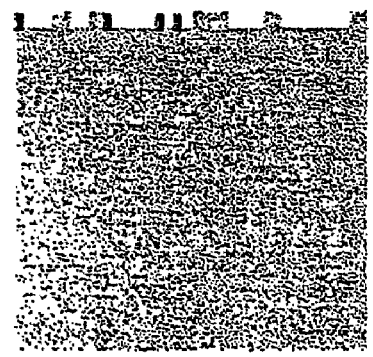

For the purpose of clarification, some of the terms used herein are described hereinbelow:

"Essentially sequence-specific agent" means an agent capable of binding to a saccharide, the binding is usually sequence-specific, i.e., the agent will bind a certain sequence of monosaccharide units only. However, this sequence specificity may not be absolute, as the agent may bind other related sequences (such as monosaccharide sequences wherein one or more of the saccharides have been deleted, changed or inserted). The agent may also bind, in addition to a given sequence of monosaccharides, one or more unrelated sequences, or monosaccharides. The essentially sequence-specific agent is usually a protein, such as a lectin, a saccharide-specific antibody or a glycosidase or glycosyltransferase. Examples of lectins include lectins isolated from the following plants:

Conavalia ensiformis
Anguilla anguilla
Triticum vulgaris
Datura stramoniuim
Galanthus nivalis
Maackia amurensis
Arachis hypogaea
Sambucus nigra
Erythrina cristagalli
Lens culinaris
Glycine max
Phaseolus vulgaris
Allomyrina dichotoma
Dolichos biflorus
Lotus tetragonolobus
Ulex europaeus
Ricinus communis In addition to the aforementioned examples of lectins, other biologically active compounds such as cytokines, chemokines and growth factors also possess the ability to bind GAGs and other polysaccharides, and hence, for the purposes of the present invention are considered to be lectins.

Examples of glycosidases include α-Galactosidase, β-Galactosidase, N-acetylhexosaminidase, α-Mannosidase, β-Mannosidase, α-Fucosidase, and the like. Some of these enzymes may, depending upon the source of isolation thereof, have a different specificity.

The above enzymes are commercially available, e.g., from Oxford Glycosystems Ltd., Abingdon, OX14 1RG, UK, Sigma Chemical Co., St. Lois, Mo., USA, or Pierce, POB. 117, Rockford, 61105 USA.

"Cleaving agent" is an essentially sequence-specific agent that cleaves the saccharide chain at its recognition sequence. Typical cleaving agents are glycosidases, including exo- and endoglycosidases, and glycosyltransferases. However, also chemical reagents capable of cleaving a glycosidic bond may serve as cleaving agents, as long as they are essentially sequence-specific. The term "cleaving agent" or "cleavage agent" is within the context of this specification synonymous with the term "essentially sequence-specific agent capable of cleaving"

"Recognition sequence" is the sequence of monosaccharides recognized by an essentially sequence-specific agent. Recognition sequences usually comprise 2-4 monosaccharide units. An example of a recognition sequence is Galβ1-3 GalNAc, which is recognized by a lectin purified from *Arachis hypogaea*. Single monosaccharides, when specifically recognized by an essentially sequence-specific agent, may, for the purpose of this disclosure, be defined as recognition sequences.

"Saccharide" is any oligo- or polysaccharide, linear or branched. This term is used hereinabove and hereinbelow different from its general meaning in the art, in that it comprises also polysaccharides, and the sugar structures of glycans, and the like.

"Mapping"—means defining a sequential order of certain predefined patterns on the polysaccharide chain, a process that results finally in obtaining the sequence of a saccharide, i.e., in complete determination of all building blocks of the saccharide.

"Sequence map" is a ordered succession of recognition sites as they occur on the saccharide.

"Monosaccharide" is a single sugar unit, such as for example a hexose, tetrose, or pentose. Specific examples of monosaccharides include Galactose (Gal), N-Acetyl-Galactosamine (GalNAc), Mannose (Man), Glucose (Glc), and the like.

In a preferred embodiment of the invention, the methods described hereinabove and illustrated hereinbelow, may be used to screen for therapeutic agents by determining the structure of therapeutically active agents or active fragments thereof. The invention is thus directed to the use of the above described method in the screening of therapeutically active agents.

In a further preferred embodiment, the analytical and mapping methods of the invention are further useful in the optimization of therapeutically active agents inasmuch as they permit the assessment of the degree of glycosylation of various therapeutically active agents, and the comparison therebetween. For example, it is well known in the art that galactose at the non-reducing end of the glycan chain may be associated with rapid clearance from the circulatory system of the glycoprotein of which said chain is an integral part. This in turn can dramatically effect the pharmokinetic parameters associated with these glycoproteins, when used as therapeutically active agents. The invention is therefore also directed to the use of the methods described hereinabove in the development and optimization of therapeutically active agents.

In another preferred embodiment, the invention is directed to the use of the methods described herein in disease diagnosis. One example of the diagnostic use of the analytical methods of the invention is the comparison and/or identification of lipopolysaccharides (LPSs) isolated from bacteria, in order to determine the identity of microbial pathogens. The comparison of different microbial LPS samples by use of the method of the present invention is illustrated hereinbelow in Example 6.

In a still further preferred embodiment, the invention is directed to the use of the methods of the invention in food and/or beverage analysis. Such analysis may include the use of the GMID method for comparing samples of food or drink with known standards, in order to determine their species origin. By way of example, the GMID analysis of milk samples of differing origin is illustrated in Example 5 hereinbelow. A further example is the detection and identification of bacterial contaminants in food and drink preparations, such as the LPS analysis described hereinbelow in Example 6.

In a further preferred embodiment, the invention provides the use of the hereinabove described methods in the analysis of genetically modified (GM) agricultural crops and the products derived therefrom. Examples of GM crops include those that produce humanized antibodies (said antibodies being glycoproteins), as well as crops that produce modified starch or other polysaccharides.

The invention provides a method for the analysis of saccharide chains. The invention uses biological reaction mechanisms, for example those involving agents that are able to recognize short oligosaccharide sequences, as well as enzymes. In contrast to prior art methods, the invention uses a multitude of reactions (i.e., an information-rich analysis). This enables the method of the invention to entirely avoid the use of the costly technologies used in most prior art methods, such as, e.g., post source decay matrix-assisted laser desorbtion/ionization mass spectrometry (PSD MALDI-MS), HPLC-MS, or fast atom bombardment coupled with mass spectrometry.

According to a preferred embodiment of the invention, after the reaction of a saccharide (labeled at the reducing end) with a first essentially sequence-specific agent, a detection step is carried out. The presence of the label indicates the presence of the recognition site a for the first essentially sequence-specific agent in the saccharide. It is important to note that this step provides the user with information concerning which of the lectin binding sites are present in the saccharide. After reaction with a second essentially sequence-specific agent, which cleaves the saccharide at its recognition sequence b, the detection step is repeated. Absence of the label shows that the sequence of the first and second recognition sites is a-b-reducing end.

In order to further illustrate the method of the invention, we now assume that the first essentially sequence-specific agent is a lectin, with a recognition site a. The saccharide to be analyzed is unlabeled. In a second step, a labeled antibody recognizing a certain saccharide sequence b is added. A detection step is now carried out, which shows whether the antibody has recognized the saccharide. In that case, all reactions, independently of the lectin used, are positive. After washing off unbound antibody, a glycosidase is added. The glycosidase has the recognition sequence c. A second detection step is carried out. In all reactions where the signal has been lost, the sequence of recognition sites must be either b-c-a or a-c-b. On the other hand, where the signal remains, the sequence of recognition sites may either be c-b-a, a-b-c, b-a-c or c-a-b.

In the above embodiment of the invention, the relation of these sites to the reducing end, is not established. However, a combination of the first above described embodiment wherein the saccharide is labeled, and of the immediately above described embodiment wherein the second essentially sequence-specific agent is labeled, will easily provide that information. Thus, in a further embodiment of the invention, the saccharide is labeled at its reducing end. It is then bound in a first step to the various lectins. In a second step, the labeled antibody is bound. The lectin and antibody are labeled by different labels which can be detected independently from each other. Thus, both labels can now be detected independently from each other, in a first and second detection step. In a third step, a glycosidase is added. A third and fourth detection step is now carried out to verify the present of both labels in each reaction. If both labels were present before addition of the glycosidase, there are a number of possibilities. First, if both labels remain after addition of the glycosidase, the sequence of recognition sites is c-a-b-reducing end. Second, if both are lost after addition of the glycosidase, the sequence of recognition sites must then be a-c-b-reducing end. Third, if the saccharide label remains and the antibody label is lost, the sequence of recognition sites must be b-c-a-reducing end.

Fourth, if the antibody label remains and the saccharide label is lost, the sequence of recognition sites may either be a-b-c-reducing end or b-a-c-reducing end.

An analogous set of reactions may be carried out wherein the saccharide is first digested with a cleaving agent, and in subsequent steps reacted with binding agents.

For example, in a preferred embodiment, a saccharide labeled at the reducing end is reacted with a first essentially sequence-specific agent, which may be a glycosidase with the recognition sequence a. In a control reaction, the labeled saccharide is left untreated. The reactions are then independently further reacted with an immobilized second essentially sequence-specific agent, which may be a lectin with the recognition sequence b. After washing off unbound saccharide, a detection step is carried out. The presence of the label indicates that site b is present in the saccharide. By comparing reactions where the first essentially sequence-specific agent was present, with independent control reactions where the first essentially sequence-specific reagent was absent, the effect of the glycosidase on the presence of the label can be determined. For instance, if the label is detected in the control reaction after binding to the lectin with recognition sequence b, but not in a reaction where the first essentially sequence-specific agent is a glycosidase with the recognition sequence a, the sequence of recognition sites is b-a-reducing end. On the other hand, if the label is present in both, control and glycosidase reactions, this indicates that the sequence of recognition sites is a-b-reducing end. The recognition site a may not be located inside the saccharide, i.e., may not exist in the saccharide sequence.

The above embodiment of the invention may be used with multiple first essentially sequence-specific agents. These are usually used in independent reactions, together with a control reaction. It is also possible to use more than one first essentially sequence-specific agent in one reaction. The multiplicity of reactions enlarges the amount of structure-related information gained.

In a further embodiment of the invention, an unlabeled saccharide is used. After digestion with a glycosidase with recognition sequence a, the saccharide is reacted with an immobilized lectin. After washing off unbound saccharide, a labeled antibody with the recognition site c is reacted with the bound saccharide fragment. Detection of the label after washing off unbound antibody indicates that c is located on the saccharide fragment that binds the lectin. The sequence of binding sites may be either c-b-a or b-c-a. The location of the reducing end with respect to the sequence of recognition sites cannot be determined with this reaction. Detection of the label in the control (without glycosidase) reaction, but not in the reaction with glycosidase, indicates that the sequence of recognition sites is b-a-c. Also in this embodiment, further independent reactions using different glycosidases, alone and/or in combination, different lectins, and/or different antibodies will enhance the amount of information gained.

It is clear that the embodiments of the invention described further above, wherein the third essentially sequence-specific agent provides the cleavage step, and the embodiments described directly above, wherein the first essentially sequence-specific agent provides the cleavage step, are substantially equivalent. A difference between both embodiments of the invention is that while in the further above described embodiments, the effect of the cleavage agent may be observed by detecting the presence of the label before reacting with the third essentially sequence-specific agent, in the directly above described embodiments a control reaction without cleavage agent must be used in order to determine the effect of said cleavage reagent. Nevertheless, the extent of information gained with the different embodiments is substantially equal, as are the methods for ordering that information and sequences of recognition sites, i.e., triplets, from it.

The above examples are based on the assumption that the saccharide is linear and the glycosidase has a recognition site within the saccharide sequence. However, the presence of a recognition site for the glycosidase within the saccharide will usually be readily verifiable from the analysis of reactions with other lectins. If any of the two labels in any reaction with a lectin is lost after addition of the glycosidase, then the glycosidase must have a recognition site within the saccharide.

As essentially sequence-specific agent, a glycosyltransferase may be used. A glycosyltransferase will add a sugar unit at a certain point in the saccharide sequence, according to a specific sequence pattern (recognition sequence). Therefore, if the monosaccharide used in the reaction is labeled, a new label can be introduced into the saccharide chain, indicating the presence of the recognition site for glycosyltransferase. Of course, the label introduced by the glycosyltransferase should be distinguishable from the other labels used.

When carrying out a set of reactions with a labeled antibody as described above, the antibody may bind in most of the reactions, but there may be very few exceptions. This is due to the possibility of overlap between saccharide recognition sequences of lectin and antibody. In such a case, the reaction with a certain lectin would be negative. This information could then be used to deduce a stretch of 3-7 sugar units, as the recognition sequences of lectin and antibody are 2-4 sugar units each.

The above described first and second detection steps may alternatively be carried out simultaneously, if there is no interference between the two detections.

As a further example, if, in a first sequence of reactions, the first reaction with a lectin occurs at site a on an end-labeled polysaccharide chain, and the second reaction with a glycosidase occurs at site b on the polysaccharide chain, the reaction with the third essentially sequence-specific agent, at site c, introduces then a second label, which can be distinguished from the first label. The presence of both labels would therefore indicate that the sequence of the three sites is either b-a-c-reducing end or b-c-a-reducing end.

On the other hand, if only the first label is detected, then two possibilities exist: (1) the recognition site for the third essentially sequence-specific agent is absent in the polysaccharide, or (2) the part of the polysaccharide containing that recognition site has been cleaved by the second essentially sequence-specific agent.

This can be verified by a second sequence of reactions wherein the second essentially sequence-specific agent is omitted or used under buffer conditions that do not allow cleavage. If, in that second sequence of reactions, the second label is not detected after reaction with the third essentially sequence-specific agent, this indicates that the third essentially sequence-specific agent lacks a binding site on the saccharide. On the other hand, presence of the second label indicates that the cleavage site is located between the site for the first and third essentially sequence-specific agent, i.e., the sequence of sites on the saccharide is c-b-a-reducing end.

In the method of the invention, there is no need to carry out these reactions one after another, the latter depending on the results of the former. Rather, the invention provides a method whereby a multitude of reactions is carried out, such that the above deductions are possible in a single set of reactions. For instance, in one set of reactions, different first essentially sequence-specific agents are used together with second and third essentially sequence-specific agents that are identical for each reaction. A second set of reactions is performed in parallel, whereby the reactions are identical with the reactions of the first set except for the second essentially sequence-specific agent, which is omitted or inactivated.

However, the information obtained in an intermediate detection step may advantageously be used to exclude certain choices of essentially sequence-specific agents in the following steps. It is clear that an essentially sequence-specific agent that does not have a recognition site on the saccharide to be analyzed would not provide information when used as a second or third essentially sequence-specific agent. In an embodiment of the invention wherein the saccharide is labeled, therefore, the results of a detection carried out after the saccharide has bound to the first essentially sequence-specific agent, may be used to chose, from the number of first essentially sequence-specific agents that have bound saccharide, the second essentially sequence-specific agent.

In yet another embodiment of the invention, the addition of a third essentially sequence-specific agent is repeated with a different agent, after the detection steps have been completed and information has been obtained as described above. For reactions in which both labels remained present after the third agent had been added for the first time, the same considerations for interpretation of the results as described above apply. In case only one of the labels remained, it can nevertheless be deduced whether the cleaving agent cuts between the recognition site of the first essentially sequence-specific agent and the recognition site of the essentially sequence-specific agent that carries the label (or the reducing end). In that case, the remaining label will also be lost after the reaction with a different third essentially sequence-specific agent.

In a further embodiment of the invention, a different second essentially sequence-specific agent may be added, which may carry a label different from or identical to the label of the second essentially sequence-specific agent added in the first set of reaction. The addition of another third essentially sequence-specific agent which cleaves the saccharide chain will then provide further information.

In a still further embodiment of the invention, two or more different second essentially sequence-specific agents are added, each with its own label, which is detectable independently of any other label used. The kind of label lost after addition of the cleaving agent will then provide information as to the position of the second essentially sequence-specific agent binding sites, similarly to the above-described considerations for experiments in which only a single second essentially sequence-specific agent is used.

As will be apparent to a person of skill in the art, by performing a sufficiently large number of reactions as set out above, a fingerprint of reactions can be obtained, which is specific to a certain saccharide. Furthermore, it is possible to "collapse" the partial sequence information obtained as outlined above into a complete sequence of the saccharide. As the number of reactions may be very large (as detailed below), the method of the invention is not, like prior art methods, limited to the analysis of oligosaccharides. It may also be used to determine the structure of polysaccharides, i.e. large saccharides with many sugar units.

In one embodiment of the invention, the first essentially sequence-specific agent is a lectin. The first essentially sequence-specific agent may also be an antibody or another sequence-specific agent.

Another embodiment of the invention provides a multitude of lectins or saccharide-specific antibodies with different sequence-specificities which are immobilized in an array on a substrate, such as a very large scale integrated (VLSI) circuit chip similar to the chips currently used to form oligonucleotide arrays. Methods for producing such chips and for binding reagents thereto are described, e.g., in WO 93/22678.

In another embodiment, the invention provides a virtual array of immobilized first essentially sequence-specific agents. An example for such a virtual array, using MASDA particles, is described in a PCT application the present inventor, IL-97/00105, which is included herein in its entirety by reference. Said first essentially sequence-specific agents are immobilized in separate reaction on MASDA particles, e.g., in 25 different reactions. Each part of the virtual array may then be reacted with either the same second essentially sequence-specific agent, this being done preferably by removing an aliquot from each MASDA reaction, mixing said aliquots, and reacting the mixture with said second essentially sequence-specific agent. If it is desired to react parts of the virtual array with different second essentially sequence-specific agents, then all MASDA reaction may be left separate, or a fraction of the virtual array may be combined in a mixture, for reaction with a single second essentially sequence-specific agent, while other parts of said virtual array are left separate for reaction with distinct second essentially sequence-specific agents. In the same way, the parts of the virtual array may also be combined or left separate for reaction with the third essentially sequence-specific agent.

Alternatively, beads may be used as immobilizing agents. A multitude of different beads for the purpose of binding peptides and proteins have been described in the art, see e.g., the Pierce catalog, p. O-222 to O-231. and T-155 to T-200. The first essentially sequence-specific agent, which is preferably a lectin, may be bound to beads. An advantage of this method is that the beads may later be divided into aliquots and reacted with different second and/or third essentially sequence-specific agents, thus further enhancing the amount of information provided by the method of the invention.

The reaction conditions for the various essentially sequence-specific agents are known in the art. Alternatively, the skilled person may easily perform a series of tests with each essentially sequence-specific agent, measuring the binding activity thereof, under various reaction conditions. Advantageously, knowledge of reaction conditions under which a certain essentially sequence-specific agent will react, and of conditions under which it remain inactive, may be used to control reactions in which several essentially sequence-specific reagents are present. For example, the second and third sequence-specific reagents may be added to the reaction simultaneously, but via a change in reaction conditions, only the second essentially sequence-specific agent may be allowed to be active. A further change in reaction conditions may then be selected in order to inactivate the second essentially sequence-specific agent and activate the third essentially sequence-specific agent. Some illustrative examples of reaction conditions are listed in the table 1 below. In addition to the pH and temperature data listed in table 1, other factor, e.g. the presence of metals such as Zn, or salts of cations such as Mn, Ca, Na, such as sodium chloride salt, may be investigated to find optimum reaction conditions or conditions under which certain essentially sequence-specific agent will be active, while others are inactive.

TABLE 1

Reaction conditions for some essentially sequence-specific agents

| codes for condition sets | Condition serial number | pH | Temp (C.) | Enzyme(s) |
|---|---|---|---|---|
| ♣ ♥ | 1 | 3.5 | 30 | Jackbean β-galactosidase |
| ♥ | 2 | 5.0 | 37 | Endo a-N Acetylgalactosidase |
| ♣ ♦ | 3 | 5.0 | 25 | α 1,2 Fucosidase β 1,2 galactosidase bovine kidney α Fucosidase |
| ♥ ♦ | 4 | 7.2 | 25 | coffee bean α galactosidase |
| ♣ ♥ ♦ | 5 | 5.8 | 55 | B. Fragilis endo β-galactosidase |
|  | 6 | 6.2 | 25 | Chicken egg lysozyme |
|  | 7 | 4.3 | 37 | Bovine testes β 1-3,4,6,Galactosidase |
|  | from Biodiversa | 2-9.5 | 50 | Gly 001-02 |
|  | from Biodiversa | 3.0-8.0 | 50 | Gly 001-04 |
|  | from Biodiversa | 2-11 | 50 | Gly 001-06 |

Symbols represent enzyme groups which are separable by external conditions.
Diversa Corp. produces Thermophilic Endo/Exo glycosidases with a wide variety of activity in various pH and Temperatures
also possible conditions could be metals and others Zn, Mn, Ca, NaCl The immobilization of the first essentially sequence-specific agent may utilize functional groups of the protein, such as amino, carboxy, hydroxy, or thiol groups. For instance, a glass support may be functionalized with an epoxide group by reaction with epoxy silane, as described in the above PCT publication. The epoxide group reacts with amino groups such as the free E-amino groups of lysine residues. Another mechanism consists in covering a surface with electrometal materials such as gold, as also described in said PCT publication. As such materials form stable conjugates with thiol groups, a protein may be linked to such materials directly by free thiol groups of cysteine residues. Alternatively, thiol groups may be introduced into the protein by conventional chemistry, or by reaction with a molecule that contains one or more thiol groups and a group reacting with free amino groups, such as the N-hydroxy succinimidyl ester of cysteine. Also thiol-cleavable cross-linkers, such as dithiobis(succinimidyl propionate) may be reacted with amino groups of a protein. A reduction with sulfhydryl agent will then expose free thiol groups of the cross-linker.

The label may be introduced into an essentially sequence-specific agent or saccharide by conventional means. Labels include any detectable group attached to the saccharide or essentially sequence-specific agent that does not interfere with its function. Labels may be enzymes, such as peroxidase and phosphatase. In principle, also enzymes such as glucose oxidase and β-galactosidase could be used. It must then be taken into account that the saccharide may be modified if it contains the monosaccharide units that react with such enzymes. Further labels that may be used include fluorescent labels, such as Fluorescein, Texas Red, Lucifer Yellow, Rhodamine, Nile-red, tetramethyl-rhodamine-5-isothiocyanate, 1,6-diphenyl-1,3,5-hexatriene, cis-Parinaric acid, Phycoerythrin, Allophycocyanin, 4',6-diamidino-2-phenylindole (DAPI), Hoechst 33258, 2-aminobenzamide, and the like. Further labels include electron dense metals, such as gold, ligands, haptens, such as biotin, radioactive labels, and the like.

Examples of labeling saccharides include:

1. Use of color labels for the reducing end (e.g. Coumarin-120)

2. Use of $^{14}C$ radioactive-labeled sugar+glycosidase (sequence specific sugar synthesis)
3. Use of $^{3}H$- radioactive-labeled sugar+glycosidase (sequence specific sugar synthesis)
4. Use of fluorescently-labeled sugar+glycosidase (sequence specific sugar synthesis)
5. Use of fluorescently-labeled lectin or mAbs
6. Use of fluorescently-labeled colored or enzyme linked mAbs
7. Use of biotin-end labeling
8. Creating a special sugar sequence and using antibodies or lectins that specifically recognize them.

The detection of enzymatic labels is well known in the art of ELISA and other techniques where enzymatic detection is routinely used. The enzymes are available commercially, e.g., from companies such as Pierce.

Fluorescent labels require an excitation at a certain wavelength and detection at a different wavelength. The methods for fluorescent detection are well known in the art and have been published in many articles and textbooks. A selection of publications on this topic can be found at p. O-124 to O-126 in the 1994 catalog of Pierce. Fluorescent labels are commercially available from Companies such as SIGMA, or the above-noted Pierce.

Coupling labels to proteins and sugars are techniques well known in the art. For instance, commercial kits for labeling saccharides with fluorescent or radioactive labels are available from Oxford Glycosystems, Abingdon, UK. Reagents and instructions for their use for labeling proteins are available from the above-noted Pierce.

Coupling is usually carried out by using functional groups, such as hydroxy, aldehyde, keto, amino, sulfhydryl, carboxylic acid, or the like groups. A number of labels, such as fluorescent labels, are commercially available that react with these groups. In addition, bifunctional cross-linkers that react with the label on one side and with the protein or saccharide on the other may be employed. The use of cross-linkers may be advantageous in order to avoid loss of function of the protein or saccharide. However, any other suitable coupling technique which permits retention of the native function of the protein or saccharide may equally be employed.

It is obvious to the skilled person, however, that a large variety of published methods may be used to couple a protein to a given support, or to couple a label to a protein or saccharide.

Detection of the label may be carried out by any suitable means as known in the art. Some detection methods are described in the above-noted WO 93/22678, the disclosure of which is incorporated herein in its entirety. Particularly suitable for the method of the present invention is the CCD detector method, described in said publication. This method may be used in combination with labels that absorb light at certain frequencies, and so block the path of a test light source to the VLSI surface, so that the CCD sensors detect a diminished light quantity in the area where the labeled agent has bound. The method may also be used with fluorescent labels, making use of the fact that such labels absorb light at the excitation frequency. Alternatively, the CCD sensors may be used to detect the emission of the fluorescent label, after excitation. Separation of the emission signal from the excitation light may be achieved either by using sensors with different sensitivities for the different wavelengths, or by temporal resolution, or a combination of both.

The present invention will now further be illustrated by the following examples.

EXAMPLE 1

Glycomolecule Analysis Using Antibodies as First and Second Sequence-Specific Agents This example further illustrates the technique of analyzing glycomolecules according to the invention. As a first and second sequence-specific agent, antibodies are used. The following tables lists the results of reactions with two different saccharides denoted for purposes of illustration, HS and NS.

The structure of the sugars is as follows:

MFLNH-II (HS):

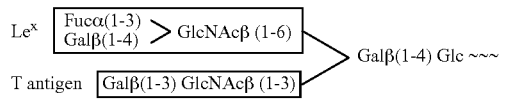

T antigen Galβ(1-3) GlcNAcβ (1-3)

NS:

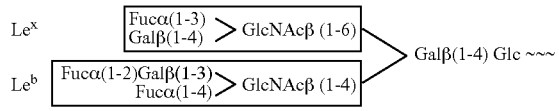

Table 2 lists the results of the reaction between the saccharide and the first and second essentially sequence-specific agents, which are antibodies against T-antigen, Lewis$^x$ (Le$^x$), or Lewis$^b$ antigen (Le$^b$). The first essentially sequence-specific agent is immobilized on a matrix, preferably a solid phase microparticle. The second essentially sequence-specific agent is labeled with a fluorescent agent, i.e., nile-red or green color. In addition, the reducing end of the saccharide is labeled, using a label clearly distinguishable from the nile-red or green color label which act as markers for the second essentially sequence-specific agents. Table 2 lists the reactions for the saccharide HS, while table 3 lists the reactions for the saccharide NS.

TABLE 2

| On the matrix | anti T-antigen | anti - Le$^x$ | anti - Le$^b$ |
|---|---|---|---|
| Saccharide bound | HS | HS | |
| Second mAb | nile-red anti-Le$^x$ | | |
| Signal | nile-red, reducing end | reducing end | none |

TABLE 3

| On the matrix | anti T-antigen | anti - Le$^x$ | anti - Le$^b$ |
|---|---|---|---|
| Saccharide bound | | NS | NS |
| Second mAb | | green anti-Le$^b$ | nile-red anti-Le$^x$ |
| Signal | | green, reducing end | nile-red, reducing end |

In summary, the following signals are now detectable in the reactions of the saccharide HS or NS (rows) when using the indicated antibodies as first essentially sequence-specific agent (columns):

TABLE 4

| On the matrix | anti T-antigen | anti - Le$^x$ | anti - Le$^b$ |
|---|---|---|---|
| HS | nile-red, reducing end | reducing end | |

TABLE 4-continued

| On the matrix | anti T-antigen | anti - Le^x | anti - Le^b |
|---|---|---|---|
| NS | | green, reducing end | nile-red, reducing end |
| NS | | green, reducing end | nile red, reducing end |

After the label has been detected and the result recorded for each reaction, a third essentially sequence-specific agent is added. In this example, two independent reactions with a third essentially sequence-specific agent are used. The solid phase carrying the sugar molecule may now be advantageously divided into aliquots, for reaction with either α1-2 Fucosidase or Exo β galactosidase (third essentially sequence-specific agents). Alternatively, three sets of reactions with a first and second essentially sequence-specific agent may be carried out.

TABLE 5 reactions after applying α1-3,4 Fucosidase:

| On the matrix | anti T-antigen | anti - Le^x | anti - Le^b |
|---|---|---|---|
| HS | | reducing end | |
| NS | | | |

TABLE 6 reaction after applying Exo β galactosidase from
D. pneumoniae (EC 3.2.1.23 catalog number 1088718 from
Boehringer Mannheim, 68298 Mannheim, Germany)

| On the matrix | anti T-antigen | anti - Le^x | anti - Le^b |
|---|---|---|---|
| HS | nile-red | | |
| NS | | green | nile-red |

TABLE 7 reactions after applying α1-2 Fucosidase:

| On the matrix | anti T-antigen | anti - Le^x | anti - Le^b |
|---|---|---|---|
| HS | nile-red, reducing end | reducing end | |
| NS | | | reducing end |

From the data gathered as explained above, a glycomolecule identity (GMID) card can now be created. An example for such information is listed in Table 8 for saccharide HS and in Table 9 for saccharide NS.

TABLE 8

| On the matrix | anti T-antigen | anti - Le^x | anti - Le^b |
|---|---|---|---|
| 0 | nile-red, reducing end | reducing end | |
| 1 | reducing end | — | — |
| 2 | nile-red | | |
| 3 | nile-red, reducing end | reducing end | |

TABLE 9

| On the matrix | anti T-antigen | anti - Le^x | anti - Le^b |
|---|---|---|---|
| 0 | | green, reducing end | nile red, reducing end |
| 1 | — | — | — |
| 2 | | green reducing end | nile red |
| 3 | | | |

The identity of the second and third essentially sequence-specific agents need not be disclosed in such a data list. For the purpose of comparison, it is sufficient that a certain code number (1, 2 or 3 in the above tables) always identifies a certain combination of reagents.

EXAMPLE 2

A Scheme for the Sequential Labeling of Reducing Ends

As has been indicated in the description and example above, the method of the invention advantageously uses labeling of the saccharide to be investigated at its reducing end. However, this labeling technique may be extended to sites within the saccharide, and thus contribute to the method of the invention, by providing more information. As it is possible to label the saccharide within the chain, by cleavage using an endoglycosidase followed by labeling of the reducing end, it is therefore possible to obtain a labeled reducing end within the saccharide chain. As that reducing end is necessarily closer to the binding sites for the first, second and third essentially sequence-specific agents, compared to the original reducing end, the use of an internally created labeled reducing end provides additional information. Moreover, it is possible, by sequentially labeling of reducing ends according to the method described further below, to identify the sites for distinct glycosidases in sequential order on the chain of the saccharide to be investigated.

The method of sequential labeling of reducing ends is now described in more detail in the following steps:

1. Blocking:

A Polysaccharide having a reducing end is incubated in a solution containing $NaBH_4$/NaOH at pH 11.5.

This treatment blocks the reducing end, so that the polysaccharide is now devoid of a reducing end (RE).

2. Exposing:

The polysaccharide of step 1 is treated with an endoglycosidase. If the recognition site for that endoglycosidase is present within the polysaccharide, a new reducing end will be created by cleavage of the polysaccharide. The solution now contains two saccharides: the fragment with the newly exposed RE in the endoglycosidase site, and the second fragment whose RE is blocked.

3: Labeling of the Reducing End

This reaction may be carried out using e.g., 2-aminobenzamide (commercially available in kit form for labeling saccharides by Oxford Glycosystems Inc., 1994 catalog, p. 62). After the reaction under conditions of high concentrations of hydrogen and in high temperature (H+/T), followed by reduction, has been completed, the mixture contains two fragments, one of which is labeled at its reducing end, while the other remains unlabeled due to the fact that its reducing end is blocked.

Another way to label reducing ends is by reductive amination. Fluorescent compounds containing arylamine groups are reacted with the aldehyde functionality of the reducing end. The resulting CH=N double bond is then reduced to a $CH_2$—N single bond, e.g., using sodium borohydride. This technology is part of the FACE (Fluorophore assisted Carbohydrate Electrophoresis) kit available from Glyko Inc., Novato, Calif., USA, as detailed e.g., in the Glyko, Inc. catalog, p. 8-13, which is incorporated herein by reference.

4. Reaction with a Second Endoglycosidase

A second endoglycosidase may now be reacted with the saccharide mixture. The new reaction mixture has now three fragments, one with an intact reducing end, a second with a reducing end labeled by 2-aminobenzimide, and a third with a blocked reducing end.

EXAMPLE 3

Derivation of Structural Information from a Series of Reactions with Essentially Sequence-Specific Agents This example further illustrates the method of the invention, i.e., the generation of data related to the structure of the saccharide by using a set of reactions as described further above. The example further demonstrates that sequence information can be deduced from said set of reactions.

In some cases, the reagents used may not react exactly as predicted from published data, e.g. taken from catalogs. For instance, the lectin Datura stramonium agglutinin as described further below is listed in the Sigma catalog as binding GlcNac. However, in the reactions detailed further below, DSA is shown to bind to Coumarin 120-derivatized Glc (Glc-AMC). It appears that Glc-AMC acts like GlcNac for all purposes, because of the structural similarity between these compounds. Further, as apparent from the results below, the endogalactosidase used cleaves not only at galactose residues, but also the bond connecting the Glc-AMC group to the rest of the saccharide It is apparent that the essentially sequence-specific agents used in the practice of the invention may in some cases have fine specificities that vary from the specificity of these agents given in published material, e.g., catalogs. Such reactions can quickly be identified by using the method of the invention with saccharides of known structure. The results found may then be compared with expected results, and the differences will allow the identification of variant specificities of the essentially sequence-specific agents used. Such variation from published data in fine specificities of essentially sequence-specific agents may then be stored for future analysis of unknown saccharides structures using these agents.

In the following, the method of the invention is illustrated using an end-labeled pentasaccharide and various lectins and glycosidases. The pentasaccharide has the structure Gal-β(1,4)[Fuc-β(1,3)]-GlcNAc-β(1,3)-Galβ(1,4)-Glc. The pentasaccharide is branched at The GlcNAc position having fucose and galactose bound to it in positions 3 and 4 respectively. The pentasaccharide is labeled at its reducing end (Glc) with Coumarin-120 (7-amino-4-methyl coumarin, available, e.g., from Sigma, catalog No. A 9891). The coupling reaction may be carried out as described above for the labeling of reducing ends by using arylamine functionalities. Coumarin-120, when excited at 312 nm emits blue fluorescence. As first and second essentially sequence-specific agents, Endo-β-Galactosidase (EG, Boehringer Mannheim) and Exo-1,3-Fucosidase (FD, New England Biolabs) are used. The reaction conditions for both reagents are as described in the NEB catalogue for Exo-1,3-Fucosidase.

Three reactions were carried out. The first included Fucosidase (FD) and Endo-Galactosidase (EG), the second, FD only, and the third, EG only. A fourth reaction devoid of enzyme served as control.

In order to ascertain that the enzymes had digested the saccharide, the various reactions are size-separated using thin-layer chromatography (TLC).

After separation, the saccharides on the TLC plate may detected by exposing the plate to ultraviolet light. The results are shown in the following illustration.

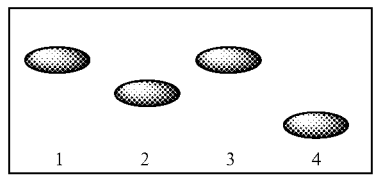

In reaction 4, no glycosidase was added, so the saccharide is intact and moves only a small distance on the plate. The fragment of reaction 2 is second in molecular weight, while the fragments of reactions 1 and 3 appear to be equal. From these data, it can be concluded that the sequence of the glycosidase sites on the saccharide is FD—EG—reducing end (coumarin-label).

The above pentasaccharide is now tested by a set of reactions as described further above. As first and second essentially sequence-specific agents, lectins were used. The lectins (*Anguilla Anguilla* agglutinin (AAA), catalog No. L4141, *Arachis Hypogaea* agglutinin (PNA), catalog No. L0881, *Ricinus communis* agglutinin (RCA I) catalog No. L9138, *Lens Culinaris* agglutinin (LCA) catalog No. L9267, *Arbus Precatorius* agglutinin, (APA). catalog No. (L9758) are available from Sigma. Lectins are also available from other companies. For instance, RCA I may be obtained from Pierce, catalog No. 33913. Lectins are immobilized by blotting onto nitrocellulose filters.

The reaction buffer is phosphate-buffered saline (PBS) with 1 mM CaCl and 1 mM MgCl. After binding of the lectins, the filter was blocked with 1% BSA in reaction buffer. As controls, reactions without lectin and with 10 μg BSA as immobilized protein were used.

The results of the reactions are indicated in Table 9. A plus indicates the presence of 312 nm fluorescence, which indicates the presence of the coumarin-labeled reducing end. The numerals 1-4 in the table indicate reactions as defined above.

TABLE 10

|   | AAA | PNA | LCA | DSA | RCA I |
| --- | --- | --- | --- | --- | --- |
| 1 |     |     |     | ++  |     |
| 2 |     | ++  |     | ++  | ++  |
| 3 |     |     |     | ++  |     |
| 4 | ++  | ++  |     | ++  | ++  |

From the results as listed in Table 9 (reaction 4-control) it is evident that lectins AAA, PNA, DSA and RCA-I bind the saccharide. Therefore, Fucose, Gal(1-3)GlcNAc, GlcNAc, and Galactose/GalNAc must be present in the saccharide, as these are the respective saccharide structures that are recognized by AAA, PNA, DSA and RCA-I. It is further evident that the above described glycosidases Fucosidase and Endo-β-Galactosidase recognize cleavage sequences in the saccharide. These sequences are Fuc(1-3/1-4) GlcNAc and GlcNAcβ(1-3)Galβ(1-3/4)Glc/GlcNAc, respectively.

It can further be deduced that both glycosidase sites are located between the fucose sugar and the reducing end, as said end is cleaved by either glycosidase when AAA (which binds to fucose) is used as immobilized lectin. The reaction with DSA, on the other hand, allows the deduction that either the GlcNAc monosaccharide is located between the glycosidase sites and the reducing end, or that Glc is directly bound to the coumarin, as neither glycosidase cleaves off the reducing end when DSA is used as immobilized agent.

Moreover, the reaction with PNA as immobilized agent shows that the reducing end is cleaved only if Endo-βGalactosidase is used (reactions 1 and 3). This indicates that the Endo-βGalactosidase site is located between the site for PNA and the reducing end. On the other hand, the Fucosidase site must be located between the PNA site and the other end of the saccharide.

When taking into account the above data, it is now possible to propose a sequence of the saccharide as follows:

Fucα(1-3,1-4)GlcNAc(1-3)Gal(1-4)Glc/GlcNAc-~~~~~reducing end

The above experiment clearly demonstrates that the method of the invention can yield a variety of data, including sequence information, based upon relatively few reactions. Some details in the sequence information may not be complete, such as the (1-3) or (1-4) connection between Fucose and GlcNAc in the above saccharide. Had the monosaccharide composition of the pentasaccharide been known, then the above analysis would have yielded all of the details of said pentasaccharide. Nevertheless, the information gained even in the absence of the monosaccharide composition data is very precise compared to prior art methods.

EXAMPLE 4

Derivation of Partial or Complete Sequence Information

The method of the invention is suitable for automation. Thus, the steps described above, for example, in examples 1 to 3, may be carried out using an automated system for mixing, aliquoting, reacting, and detection. The data obtained by such an automated process may then be further processed in order to "collapse" the mapping information to partial or complete sequence information. The method for such data processing is described in further detail below.

After all data have been collected, a comparison is made between detection signals obtained from reactions prior to the addition of glycosidase, to signals obtained after the addition (and reaction with) of glycosidase. Those signals that disappear after reaction with glycosidase are marked. This may advantageously be done by preparing a list of those signals, referred to hereinafter as a first list. The identity of two sites on the polysaccharide may now be established for each such data entry. The position in the (optionally virtual) array indicates the first essentially sequence-specific agent. If a signal has been detected before reaction with the glycosidase, the recognition site for that agent must exist in the polysaccharide. The disappearance of a signal, for instance, of the signal associated with the second essentially sequence-specific agent, now indicates that the glycosidase cleaves between the recognition sites of the first and second essentially sequence-specific agents. The sequence of recognition sites is therefore (first essentially sequence-specific agent)-(glycosidase)-(second essentially sequence-specific agent). If the signal for the reducing end is still present after digestion with the glycosidase, then the relative order of the recognition sequences with respect to the reducing end can be established; otherwise, both possibilities (a-b-c and c-b-a) must be taken into account. For the purpose of illustration, the term "recognition site of the first essentially sequence-specific agent" shall be denoted in the following "first recognition site", the term "recognition site for the second essentially sequence-specific agent" shall be denoted "second recognition site", and the term "recognition site for glycosidase" shall be denoted "glycosidase".

It is now possible to create a second list of triplets of recognition sites of the above type (type 1 triplets):

(first recognition site)-(glycosidase)-(second recognition site).

By the same token, a third list can now be created relating to (optionally virtual) array locations where all signals remain after addition of glycosidase (type 2 triplets):

(glycosidase)-(first recognition site)-(second recognition site)

Obviously, a sufficient number of triplets defines a molecule in terms of its sequence, i.e., there can only be one sequence of saccharides that will contain all of the triplets found. A lower number of triplets may be required when information on the length of the molecule is available. The number of required triplets may be even lower if the total sugar content of the molecule is known. Both saccharide molecular weight and total monosaccharide content may be derived from prior art methods well known to the skilled person.

The process of obtaining sequence information, i.e., of collapsing the triplets into a map of recognition sites, is described below.

The second and third lists of triplet recognition sites are evaluated for identity (three out of three recognition sites identical), high similarity (two out of three recognition sites identical), and low similarity (one out of three recognition sites identical). For the purposes of illustration, it is now assumed that the polysaccharide is a linear polysaccharide, such as, for example, the saccharide portion of the glycan Heparin.

The above second and third lists are then used to prepare therefrom a set of lists of triplets wherein each list in said set of lists contains triplets that share the same glycosidase recognition sequence. By comparing all triplets containing a certain glycosidase recognition sequence with all triplets containing a second glycosidase recognition sequence, it is now possible to divide the polysaccharide sequence into four areas, ranging from the first end of the molecule to glycosidase 1 (fragment a), from glycosidase 1 to glycosidase 2 (fragment b), and from glycosidase 2 to the second end of the molecule (fragment c):

<first end><glycosidase 1><glycosidase2><second end>

Identical recognition sites within triplets of type 2 with different glycosidase sites, wherein said recognition sites are located in the same direction in relation to the respective glycosidase site, are candidates for the location within either the area a or c, depending on said location. Identical recognition sites within triplets of type 2 with different glycosidase sites, wherein said recognition sites are located in different directions (e.g., one in the direction of the reducing end, in the other triplet, in the direction of the non-reducing end), are candidates for the location within the area b, i.e., between the two glycosidase sites.

Identical recognition sites within triplets of type 1 with different glycosidase sites are candidates for the location of one of the first or second recognition sites in area a (or c), and the other of said first or second recognition sites being located in the area c (or a). That is, if one of the first or second recognition sites is located in area a, then the other of said first or second recognition sites must be located in area b, and vice versa. None of the said first or second recognition sites may be located in area b.

Identical recognition sites within triplets of type 1 with different glycosidase sites, wherein a given recognition site is located in one of the triplets, in the direction of the reducing end and in the other triplet, in the direction of the non-reducing, are candidates for the location of said recognition site within area b.

Having established the above positional relationships for a number of recognition sites within the triplets, the total of the recognition sequences can now be arranged in a certain order using logical reasoning. This stage is referred to as a sequence map. If a sufficient number of recognition sequences are arranged, the full sequence of the saccharide may be derived therefrom. As the method does not determine the molecular weight of the saccharide, the chain length is unknown. Therefore, if the degree of overlap between the various recognition sites is insufficient, there may be regions in the sequence where additional saccharide units may be present. Such saccharide units may be undetected if they do not fall within a recognition site of any of the essentially sequence-specific agents used. However, the entire sequence information may also be obtained in this case, by first obtaining the molecular weight of the saccharide, which indicates its chain length, and secondly its total monosaccharide content.

Another possibility of closing gaps in the sequence map is the method of example 2, wherein sequential degradation by glycosidase is employed to derive sequence information.

The existence of branching points in the saccharide may complicate the method as outline above. One remedy to that is to use glycosidases to prepare fractions of the molecule, and analyze these partial structures. The extent of branching in such partial structures is obviously lower than in the entire molecule. In addition, reagents may be employed that specifically recognize branching points. Examples for such reagents are e.g., the antibodies employed in example 1 above. Each of these antibodies binds a saccharide sequence that contains at least one branching point. Moreover, certain enzymes and lectins are available that recognize branched saccharide structures. For instance, the enzyme pullanase (EC 3.2.1.41) recognizes a branched structure. In addition, antibodies may be generated by using branched saccharide structures as antigens. Moreover, it is possible to generate peptides that bind certain saccharide structures, including branched structures (see e.g., Deng S J, MacKenzie C R, Sadowska J, Michniewicz J, Young N M, Bundle D R, Narang; Selection of antibody single-chain variable fragments with improved carbohydrate binding by phage display. J. Biol. Chem. 269, 9533-38, 1994).

In addition, knowledge of the structure of existing carbohydrates will in many cases predict accurately the existence of branching points. For instance, N-linked glycans possess a limited number of structures, as listed at p. 6 of the oxford Glycosystems catalog. These structures range from monoantennary to pentaantennary. The more complicated structures resemble simpler structures with additional saccharide residues added. Therefore, if monoantennary structure is identified, it is possible to predict all of the branching points in a more complicated structure, simply by identifying the additional residues and comparing these data with a library of N-linked glycan structures.

Moreover, it will often be possible by analyzing data gathered according to the method of the invention, to deduce the existence and location of branching points logically. For instance, if two recognition sites, denoted a and b, are located on different branches, then digesting with a glycosidase whose site is located between the reducing end and the branching point will result in loss of the reducing end marker. The markers for both recognition sites a and b, however, will remain. If a glycosidase located between the branching point and recognition site a is used, then the marker for recognition site b and the reducing end marker will be cleaved off. Not taking into account the possibility of branching points, this would indicate that the recognition site b is located between the recognition site a and the reducing end. However, if a glycosidase located between the recognition site b and the branching point is used, the reducing end marker and recognition site a will be cleaved off. Again, not taking into account the possibility of branching, this would indicate that recognition site a is located between the reducing end and recognition site b. These deductions are obviously incompatible with one another, and can only be resolved if one assumes that recognition sites a and b are located on two different branches. The branching point is located between the recognition sites a and b and the first of the above glycosidases. The other above glycosidases used are located on a branch each, between the branching point and the respective recognition site (a or b).

Therefore, when using agents that recognize branched structures in the method of the invention, as essentially sequence-specific agents, it is possible to derive information on the existence and location of branching points in the saccharide molecule. This information can then be used to construct sequence maps of each branch of the structure, yielding a sequence map of the entire branched structure. The gaps in such a structure may then be closed as in the case of unbranched saccharides, according to the invention, i.e., by using additional reactions, by digestion with glycosidases, whereby the regions of the molecule where gaps exist are specifically isolated for further analysis according to the method of the invention, and by sequential glycosidase digestion as described further above.

In summary, a method for determining the sequence of a saccharide and/or for mapping the structure of said saccharide according to the invention comprises the steps of:

1. collecting triplets of type 1 and type 2
2. sorting said triplets according to similarity
3. comparing triplets with different glycosidase recognition sites
4. arranging the triplets in the order of occurrence on the saccharide
5. arranging the glycosidase recognition sites
6. Checking the compatibility to the triplets
7. Arranging recognition sequences of glycosidases and of first and second essentially sequence-specific agents in a single file order
8. Translating the recognition sequences (sites) into polysaccharide sequence
9. correcting "overlap" problems
10. outputting a sequence
11. Checking against all available data After the above step 5 has been carried out, a preliminary order of glycosidase sites has been established. In step 6, it is now checked for each triplet whether predictions based thereon are in agreement with that order. Then, based on contradiction in the data, a new model is generated that fits the data of the triplet. This model is then tested against the data of all triplets. Furthermore, additional reactions may be carried out, in order to extract additional vectorial information regarding the recognition sites that involve said triplet.

After the above step 8, wherein the sequentially arranged recognition sites are translated into a sequence of actual monosaccharide units, a model of the saccharide sequence can be suggested. In order to test said model, a number of questions needs to be answered. The first of these is, what is the minimum sequence that would still have the same sequence map? At this stage, information on molecular weight and monosaccharide composition, if available, is not taken into account. This approach merely serves the creation of a sequence which incorporates all of the available data with as few as possible contradictions. In that respect, the second question to be answered is, does the minimum sequence still agree with all of the data available at that point (excluding optional molecular weight and monosaccharide composition data)? The third question to be answered is, do other sequences exist that would fit the sequence map as established? In the affirmative, the additional sequences may then be tested using the question: How does each sequence model agree with the triplet information, and with additional optional data, such as information on the molecular weight, monosaccharide composition, and model saccharide structures known from biology.

Finally, the sequence model that has been found to be best according to the steps 1-10 described above, will then be tested against all triplets, monosaccharide composition, prior knowledge on the molecular weight and structural composition of the saccharide, and predictions from biologically existent similar structures. By such repeated testing, the contradictions between the available data and the sequence model are identified, and if possible, the sequence model is adapted to better represent the data.

EXAMPLE 5

Glyeomolecule Identity (GMID) Analysis of Milk Samples

The aim of this example is to demonstrate the application of the GMID technique to the analysis and comparison of milk samples.

A. Membranes and 1$^{st}$ Layer Lectins:

The supporting surface used in the experiments described hereinbelow is a nitrocellulose membrane. The membranes were prepared as follows:

1. Nitrocellulose membranes were cut out and their top surface marked out into an array of 9×6 squares (3mm$^2$ each square). The membranes were then placed on absorbent paper and the top left square of each one marked with a pen.

2. Lyophilized lectins were resuspended in water to a final concentration of 1 mg/ml. The resuspended lectins (and a control solution: 5% bovine serum albumin) were vortex mixed and 1 µl of each solution is added to one of the 28 squares on the blot, indicated by shading in the following illustrative representation of a typical blot:

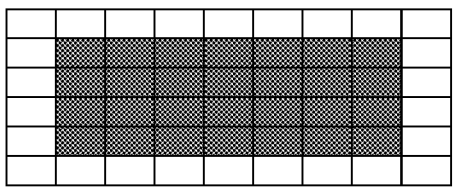

The lectins used in this experiment are listed in Table 11.

TABLE 11

| Lectin | Manufacturer | Cat. No. |
|---|---|---|
| WGA | Vector | MK2000 |
| SBA | Vector | MK2000 |
| PNA | Vector | MK2000 |
| DBA | Vector | MK2000 |
| UEA I | Vector | MK2000 |
| CON A | Vector | MK2000 |
| RCA I | Vector | MK2000 |
| BSL I | Vector | MK3000 |
| SJA | Vector | MK3000 |
| LCA | Vector | MK3000 |
| Swga | Vector | MK3000 |
| PHA-L | Vector | MK3000 |
| PSA | Vector | MK3000 |
| AAA | — | — |
| PHA-E | Vector | MK3000 |
| PNA | Leuven | LE-408 |
| LCA | Sigma | L9267 |
| DSA | Sigma | L2766 |
| APA | | — |
| WGA | Leuven | LE-429 |
| Jacalin | Leuven | LE-435 |
| 5% BSA | Savyon | M121-033 |

3. The prepared blots were placed in 90 mm petri dishes.

4. The blots were blocked by adding to each petri dish 10 ml of any suitable blocking solution well known to the skilled artisan (e.g. 5% bovine serine albumin).

5. The dishes containing the blots in the blocking solution were agitated gently by rotation on a rotating table (50 rpm) for 2 hours at room temperature (or overnight at 4° C., without rotation).

6. The blots were then washed by addition of 10 ml washing solution to each petri dish. Any commonly available buffered solution (e.g. phosphate buffered saline) may be used for performing the washing steps. The dishes were washed by rotating gently (50 rpm) for 5 minutes. The procedure was performed a total of three times, discarding the old washing solution and replacing with fresh solution each time.

B: Addition of Milk Samples:

The milk samples used were as follows:
1. Bovine UHT long-life milk (3% fat) obtained from Ramat haGolan dairies, Israel (lot 522104);
2. Pasteurized goat's milk, obtained from Mechek dairies, Israel (lots 1 and 2);
3. Non-pasteurized goat's milked obtained as in 2. (lots 3 and 4).

The milk samples were diluted to 10 % v/v and approximately 5 ml of each sample applied to separate blots.

Duplicate blots were prepared for each of the aforementioned milk samples. In addition a further pair of blots were prepared without the addition of saccharides (negative control).

The blots were then incubated at room temperature with agitation for one hour.

C. Colored Lectins:

From prior knowledge of the monosaccharide composition of the milks tested, and by application of a computer program based on the algorithm described hereinbelow in Example 7, the following colored lectins were chosen: Con A, VVA.

A mixture of these two lectins was prepared in washing solution, such that the concentration of each colored lectin was 2 mg/ml.

500 µl of each lectin mix was incubated on the blots prepared as described above. Each blot was read both by measuring the fluorescence of fluorescein at 520 nm, and, in the case of the biotinylated lectin, measuring the signal of the TMB blue color produced following reaction of biotin with an HRP-streptavidin solution The results obtained for the FITC-labeled and biotin-labeled lectins are given in Tables 12 and 13, respectively. The results presented in these tables are measured on a 0 to 3 scale, wherein 0 represents a signal that is below the noise level, and wherein results of 1-3 represent positive signals (above noise) following subtraction of the results obtained in the no-saccharide control.

Glycomolecule identity (GMID) cards obtained from these results for pasteurized goat's milk (lots 1 and 2), non-pasteurized goat's milk (lots 3 and 4) and bovine milk are shown in FIG. 1 (A to E, respectively). The positions of lectins 1 to 24 are shown in one row from left to right at the top of each card 1.

D. Interpretation of Results:

The bovine milk sample yielded a GMID indicating that the polysaccharide in the sample contains saccharides that yield positive results for lectins specific for:
a. glucose/mannose (ConA, PSA and LCA);
b. GlcNac (WGA and DSA).

The pasteurized goat milk samples yielded positive results for:
a. glucose/mannose (conA, PSA and LCA);
b. GlcNac (DSA).

No difference in lectin reactivity between the lots tested was observed.

The non-pasteurized goat milk sample gave a positive reaction for:
a. glucose/mannose (ConA, PSA and LCA);
b. GlcNac (DSA).

Figure 3:
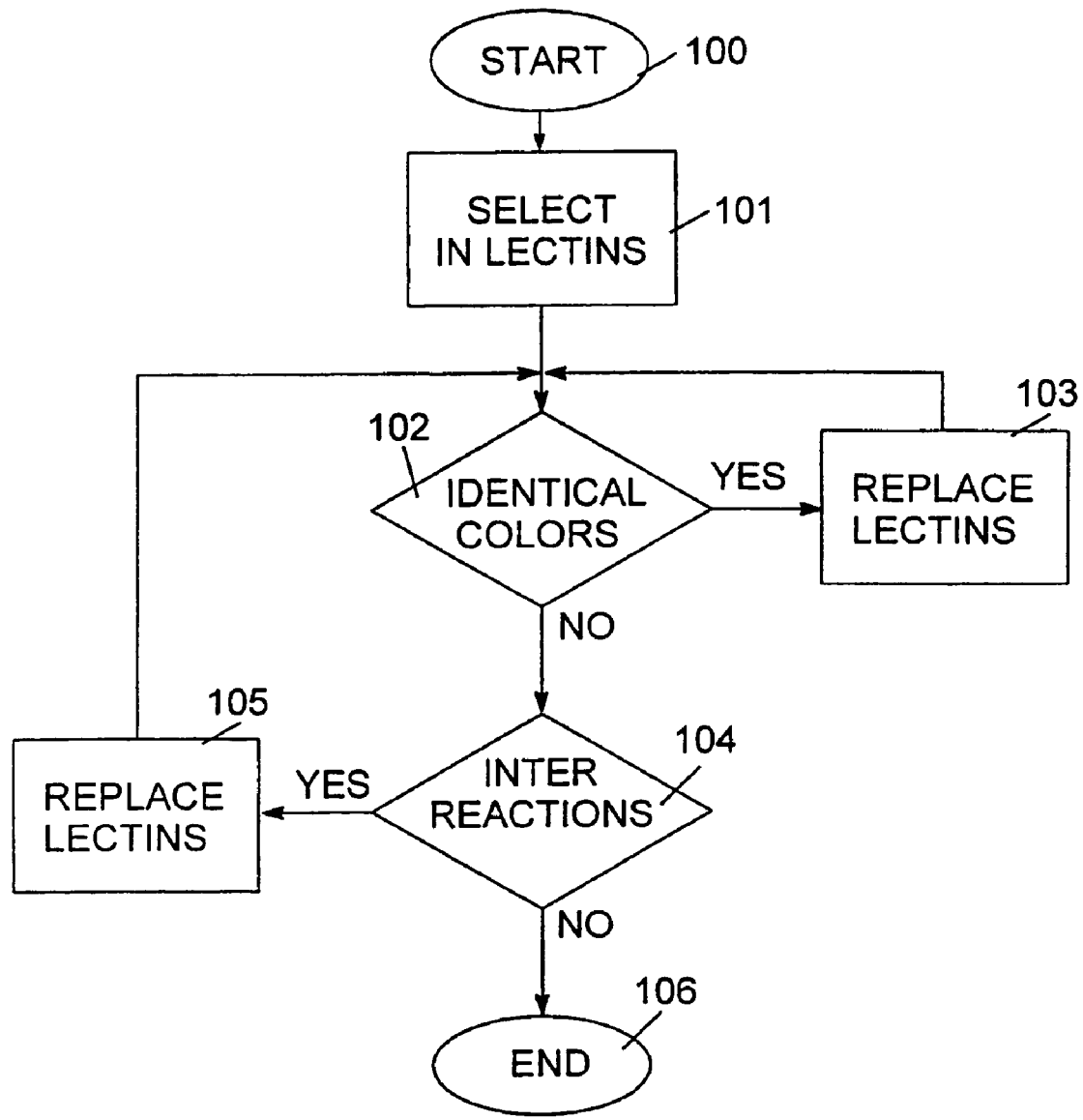
FIG. 3 is a high-level logic flowchart that illustrates an algorithm for choosing a set of colored lectins.

In summary, the bovine milk differed from the goat's milk in that only the former reacted with WGA. There was essentially no difference between the pasteurized and non-pasteurized goat's milk samples, with the exception that the signal intensity was significantly lower in the pasteurized samples.

for the need to reduce interactions between lectins. A flow chart illustrating an algorithm for use in colored marker selection is shown in FIG. 3. The algorithm shown in FIG. 3 begins with the selection of n colored lectins (or other detectable markers) 101, said initial selection being made in accordance

TABLE 12

| | Lectins Sample | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Control | 0 | 3 | 0 | 3 | 2 | 0 | 3 | 3 | 0 | 0 | 2 | 2 | 2 | 0 | N/A | 0 | 0 | 1 | N/A | N/A | N/A | N/A | 0 | 1 |
| Control | 0 | 3 | 0 | 3 | 2 | 0 | 3 | 3 | 0 | 0 | 2 | 2 | 2 | 0 | " | 0 | 0 | 1 | " | " | " | " | 0 | 1 |
| 3% Bovine | 1 | 3 | 0 | 3 | 2 | 1 | 3 | 3 | 1/0 | 1 | 2 | 2 | 2 | 0 | " | 0 | 1 | 3 | " | " | " | " | 1 | 1 |
| 3% Bovine | 1 | 3 | 0 | 3 | 2 | 1 | 3 | 3 | 1/0 | 1 | 2 | 2 | 2 | 0 | " | 0 | 1 | 3 | " | " | " | " | 1 | 1 |
| #1 Goat Past. | 1 | 3 | 0 | 3 | 2 | 0 | 3 | 3 | 1/0 | 1 | 2 | 2 | 2 | 0 | " | 0 | 0 | 2 | " | " | " | " | 0 | 1 |
| #1 Goat Past. | 1 | 3 | 0 | 3 | 2 | 0 | 3 | 3 | 1/0 | 1 | 2 | 2 | 2 | 0 | " | 0 | 0 | 2 | " | " | " | " | 1 | 1 |
| #2 Goat Past. | 1 | 3 | 0 | 3 | 2 | 0 | 3 | 3 | 1/0 | 1 | 2 | 2 | 2 | 0 | " | 0 | 0 | 2 | " | " | " | " | 0 | 1 |
| #2 Goat Past. | 1 | 3 | 0 | 3 | 2 | 0 | 3 | 3 | 1/0 | 1 | 2 | 2 | 2 | 0 | " | 0 | 0 | 2 | " | " | " | " | 0 | 1 |
| #3 Goat not Past. | 2 | 3 | 0 | 3 | 2 | 0 | 3 | 3 | 1 | 2 | 2 | 2 | 2 | 0 | " | 0 | 1 | 2 | " | " | " | " | 0 | 1 |
| #3 Goat not Past. | 2 | 3 | 0 | 3 | 2 | 0 | 3 | 3 | 1 | 2 | 2 | 2 | 2 | 0 | " | 0 | 1 | 2 | " | " | " | " | 0 | 1 |
| #4 Goat not Past. | 2 | 3 | 0 | 3 | 2 | 0 | 3 | 3 | 1 | 2/1 | 2 | 2 | 2 | 0 | " | 0 | 1 | 2 | " | " | " | " | 0 | 1 |
| #4 Goat not Past. | 2 | 3 | 0 | 3 | 2 | 0 | 3 | 3 | 1 | 2/1 | 2 | 2 | 2 | 0 | " | 0 | 1 | 2 | " | " | " | " | 0 | 1 |

TABLE 13

| | Lectins Sample | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Control | 0 | 1/0 | 0 | 1 | 1 | 0 | 1 | 1 | 0 | 0 | 1 | 1 | 1/0 | 0 | N/A | 0 | 0 | 1/0 | N/A | N/A | N/A | N/A | 0 | 0 |
| Control | 0 | 1/0 | 0 | 1 | 1 | 0 | 1 | 1 | 0 | 0 | 1 | 1 | 1/0 | 0 | " | 0 | 0 | 1/0 | " | " | " | " | 0 | 0 |
| 3% Bovine | 2 | 2 | 0 | 2 | 1 | 2 | 2 | 2 | 1 | 2 | 1 | 1 | 1 | 1 | " | 0 | 2 | 2 | " | " | " | " | 2 | 2 |
| 3% Bovine | 2 | 2 | 0 | 2 | 1 | 2 | 2 | 2 | 1 | 2 | 1 | 1 | 1 | 1 | " | 0 | 1/0 | 2 | " | " | " | " | 2 | 2 |
| #1 Goat Past. | 2 | 2 | 0 | 2 | 1 | 2 | 2 | 2 | 1 | 2 | 1 | 1 | 1 | 1 | " | 0 | 0 | 2 | " | " | " | " | 1 | 2 |
| #1 Goat Past. | 2 | 2 | 0 | 2 | 1 | 2 | 2 | 2 | 1 | 1 | 1 | 1 | 1 | 1 | " | 0 | 0 | 2 | " | " | " | " | 1 | 2 |
| #2 Goat Past. | 2 | 2 | 0 | 2 | 1 | 2 | 2 | 2 | 1 | 1 | 1 | 1 | 1 | 1 | " | 0 | 0 | 2 | " | " | " | " | 1 | 2 |
| #2 Goat Past. | 2 | 2 | 0 | 2 | 1 | 1 | 2 | 2 | 1 | 1 | 1 | 1 | 1 | 0 | " | 0 | 0 | 2 | " | " | " | " | 1 | 2 |
| #3 Goat not Past. | 2 | 2 | 0 | 2 | 1 | 1 | 2 | 1 | 1 | 1 | 1 | 1 | 1 | 0 | " | 0 | 0 | 2 | " | " | " | " | 0 | 2 |
| #3 Goat not Past. | 2 | 2 | 0 | 2 | 1 | 1 | 2 | 1 | 1 | 1 | 1 | 1 | 1 | 0 | " | 0 | 0 | 2 | " | " | " | " | 0 | 2 |
| #4 Goat not Past. | 2 | 2 | 0 | 2 | 1 | 1 | 2 | 1 | 1 | 1 | 1 | 1 | 1 | 0 | " | 0 | 0 | 2 | " | " | " | " | 0 | 2 |
| #4 Goat nol Past. | 2 | 2 | 0 | 2 | 1 | 1 | 2 | 1 | 1 | 1 | 1 | 1 | 1 | 0 | " | 0 | 0 | 2 | " | " | " | " | 0 | 2 |

EXAMPLE 6

Glyeomolecule Identity (GMID) Analysis of Lipopolysaccharides

A GMID analysis was performed on five different bacterial lipopolysaccharides obtained from Sigma Chemical Co. (St. Louis, Mo., USA)(LPS#1, 7, 10, 15 and 16), essentially using the method as described in Example 5, above. The colored lectins used were ECL, WGA, VVA and SBA.

Figure 2:
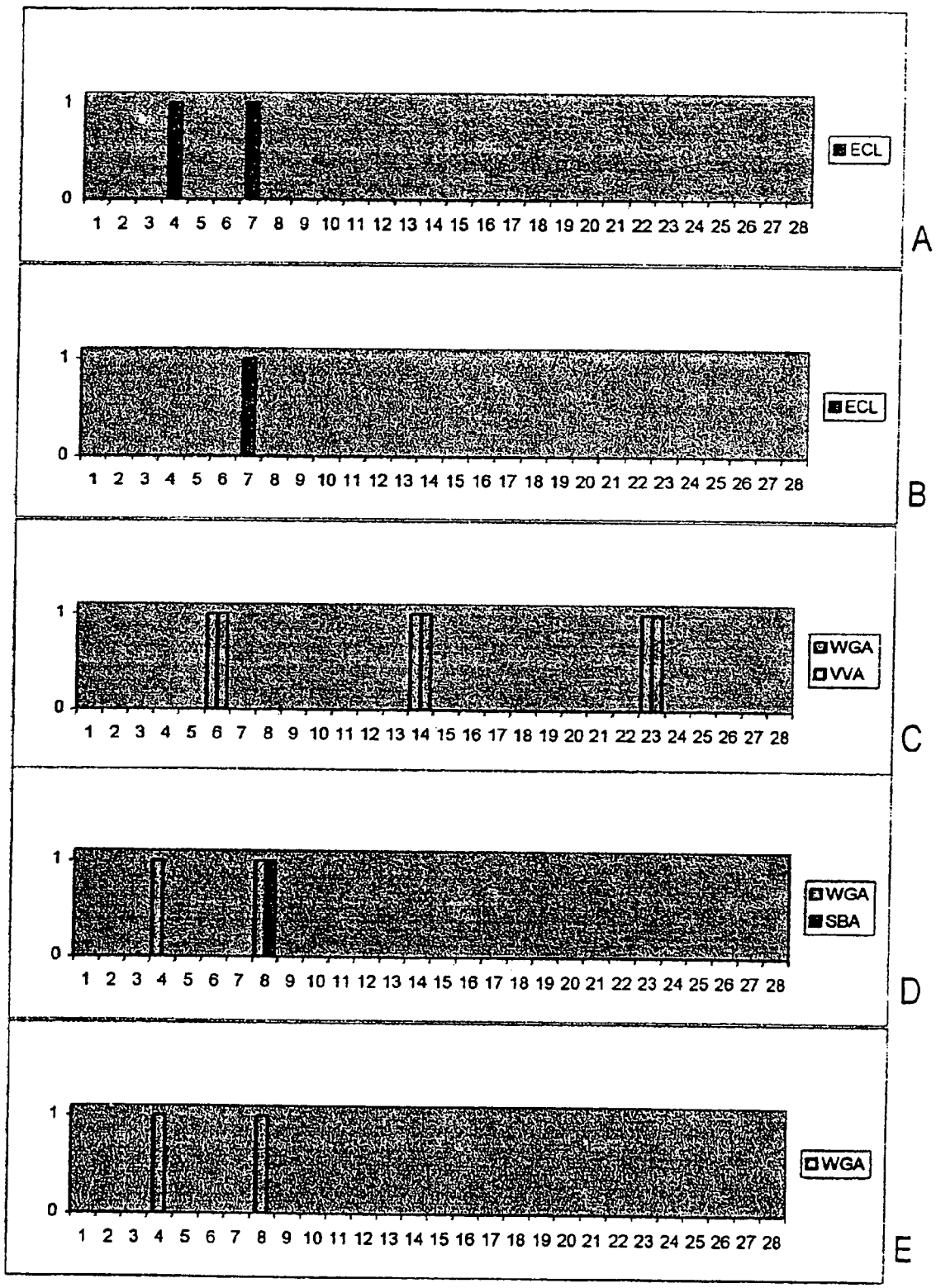
FIG. 2 is a reproduction of the GMID cards obtained for various lipopolysaccharide samples. Cards A to E correspond to LPS# 1, 7, 10, 15 and 16 respectively.

The GMID cards obtained for samples LPS# 1, 7, 10, 15 and 16 are shown in FIG. 2 (A to E, respectively). It may be seen from this figure that the GMID cards provide unique "fingerprints" for each of the different lipopolysaccharides, and may be used for identifying the presence of these compounds in samples containing bacteria or mixtures of their products.

EXAMPLE 7

Method for Selecting Colored Lectins

A number of factors must be taken into consideration when selecting colored lectins for use in the method of polysaccharide analysis illustrated in Examples 5 and 6. Among these considerations are the need for each of the chosen lectins to have a distinguishable color or other detectable marker, and with information obtained about the partial or full monosaccharide composition of the saccharide to be analyzed. In the next step 102, the colors of the selected lectins are examined in order to check for identity/non-identity of the colors selected. If there are identical colors in the selected group, then the process proceeds to step 103, otherwise the flow proceeds with step 104. In step 103, one of the lectins that has been found to have a non-unique color is replaced by another lectin that belongs to the same binding category (that is, one that has the same monosaccharide binding specificity); the flow proceeds to step 102. In step 104, the n selected lectins are tested in order to detect any cross-reactivity with each other, and with the non-colored lectins used in the first stage of the method described hereinabove in Example 5. If cross-reactivity is found, then the process continues to step 105, otherwise the flow proceeds to step 106, where the algorithm ends. In step 105, one of the lectins determined to cross-react with another lectin is replaced by a lectin which does not cross-react; the flow then proceeds to 102. The algorithm ends with step 106.

It is to be emphasized that while for values of n which are small, and for saccharides with a simple monosaccharide composition, the above-described algorithm may be applied by the operator himself/herself manually working through each step of the selection procedure. Alternatively (and especially for cases where n is a larger number or the monosaccharide composition is more complex), the algorithmic processes described hereinabove may be performed by a computer program designed to execute said processes.

The above examples have demonstrated the usefulness of the method described herein. However, they have been added for the purpose of illustration only. It is clear to the skilled person that many variations in the essentially sequence-specific agents used, in the reaction conditions therefor, in the technique of immobilization, and in the sequence of labeling, reaction and detection steps may be effected, all without exceeding the scope of the invention.

What is claimed is:

1. A method for the structural analysis of a saccharide, comprising:
   a) providing on a surface a plurality of essentially sequence- and/or site-specific saccharide binding agents;
   b) contacting said surface with a saccharide to be analyzed, or with a mixture comprising a plurality of fragments of said saccharide;
   c) washing or otherwise removing unbound saccharide or saccharide fragments from said surface;
   d) adding to the surface obtained in step c) an essentially sequence- and/or site-specific saccharide binding marker, or a mixture of essentially sequence- and/or site-specific saccharide binding markers;
   e) acquiring one or more images of the markers that are bound to said surface; and
   f) generating a map from said one or more images and thereby deriving structural information of said saccharide.

2. A method according to claim 1, wherein the markers are chromogenic binding agents, and wherein the images of the markers are colors that develop on the surface.

3. A method according to claim 1, wherein step f) comprises visual inspection of the surface and comparison with a standard.

4. A method according to claim 1, wherein step f) comprises the use of optical filters.

5. A method according to claim 1, wherein step e) comprises photographing and/or digitizing the image.

6. A method according to claim 1, wherein the essentially sequence- and/or site-specific binding agents are lectins.

7. A method according to claim 1, wherein the essentially sequence- and/or site-specific binding agents are antibodies.

8. A method according to claim 2, wherein the essentially sequence- and/or site-specific chromogenic binding agents are colored lectins.

9. A method according to claim 2, wherein the essentially sequence- and/or site-specific chromogenic binding agents are fluorescent lectins.

10. A method according to claim 2, wherein the essentially sequence- and/or site-specific chromogenic binding agents are biotin-labeled lectins.

11. A method according to claim 2, wherein the essentially sequence- and/or site-specific chromogenic binding agents are fluorescent antibodies.

12. A method according to claim 2, wherein the essentially sequence- and/or site-specific chromogenic binding agents are biotin-labeled antibodies.

13. A method according to claim 2, wherein the essentially sequence- and/or site-specific chromogenic binding agents are enzyme-labeled antibodies.

14. A method according to claim 1, further comprising treating the saccharide with an essentially sequence-specific agent capable of cleaving the saccharide chain.

15. A method according to claim 14, wherein the saccharide is treated before being contacted with the surface.

16. A method according to claim 14, wherein the saccharide is treated after removal of unbound saccharide, but before adding the essentially sequence-specific chromogenic binding agents.

17. A method according to claim 1, wherein the surface is a filter paper, and wherein the essentially sequence-specific agents are arranged in a pre-defined order on said filter paper.

18. A glycomolecule identity (GMID) card, listing saccharide structural analysis data obtained according to claim 17.

19. The GMID card according to claim 18, wherein the essentially sequence-specific reagents used are represented by code numbers.

20. The GMID card according claim 18, wherein combinations of essentially sequence-specific reagents used in the analysis are represented by unique code numbers.

21. A method for the structural analysis of a saccharide, comprising:
   a) providing on a surface a plurality of essentially sequence- and/or site-specific saccharide binding agents;
   b) contacting said surface with a saccharide to be analyzed, or with a mixture comprising a plurality of fragments of said saccharide;
   c) washing or otherwise removing unbound saccharide or saccharide fragments from said surface;
   d) adding to the surface obtained in step c) an essentially sequence- and/or site-specific saccharide binding marker, or a mixture of essentially sequence- and/or site-specific saccharide binding markers;
   e) acquiring one or more images of the markers that are bound to said surface; and generating a map from said one or more images;
   f) obtaining sequence information of the saccharide from said image map; and
   g) deriving structural information of said saccharide from said sequence information.

* * * * *